United States Patent
Lim et al.

(10) Patent No.: US 7,308,312 B1
(45) Date of Patent: *Dec. 11, 2007

(54) SETSCREW RETENTION IN CONNECTOR BLOCK FOR IMPLANTABLE MEDICAL DEVICE

(75) Inventors: Wisit Lim, Palmdale, CA (US); Russell Bruch, Greenville, SC (US)

(73) Assignee: Pacesetter, Inc., Sylmar, CA (US)

( * ) Notice: Subject to any disclaimer, the term of this patent is extended or adjusted under 35 U.S.C. 154(b) by 262 days.

This patent is subject to a terminal disclaimer.

(21) Appl. No.: 11/072,805

(22) Filed: Mar. 3, 2005

(51) Int. Cl.
*A61N 1/08* (2006.01)
*A61N 1/372* (2006.01)

(52) U.S. Cl. .......................... 607/37; 607/36; 439/362
(58) Field of Classification Search ................. 607/36, 607/37; 439/909, 814; 279/18; 292/43, 292/55; D08/387; 403/362
See application file for complete search history.

(56) References Cited

U.S. PATENT DOCUMENTS

| | | | |
|---|---|---|---|
| 4,072,154 A * | 2/1978 | Anderson et al. ............. | 607/37 |
| 4,316,471 A * | 2/1982 | Shipko et al. ................. | 607/37 |
| 5,000,177 A | 3/1991 | Hoffmann et al. ....... | 128/419 P |
| 5,176,136 A | 1/1993 | Giele ....................... | 128/419 P |
| 5,509,928 A | 4/1996 | Acken ........................... | 607/37 |
| 5,534,019 A | 7/1996 | Paspa | |
| 5,989,077 A | 11/1999 | Mast et al. .................. | 439/814 |
| 7,155,283 B2 * | 12/2006 | Ries et al. ..................... | 607/37 |
| 2004/0225334 A1 | 11/2004 | Persuitti et al. ............... | 607/37 |

FOREIGN PATENT DOCUMENTS

WO WO 99/46003 9/1999

* cited by examiner

*Primary Examiner*—Carl Layno
*Assistant Examiner*—Tammie K. Heller

(57) ABSTRACT

A header assembly for coupling a medical electrical lead to a medical stimulating device includes a header having a first bore for receiving a proximal terminal pin of the lead. A connector block coupled to the header has a second bore aligned with the first bore and a tapped bore transverse of, and in communication with, the second bore, and the assembly includes a setscrew with mounting threads of defined length threadedly engaged with the tapped bore. The tapped bore has first and second tapped regions spaced by a smooth bore region which is longer than the length of the threaded portion of the setscrew. As the setscrew is tightened, it has already been threaded through the first tapped region and resides within the smooth bore region, and then becomes threadedly engaged with the second tapped region such that the tip end becomes firmly engaged with the proximal terminal pin of the lead.

13 Claims, 5 Drawing Sheets

SETSCREW RETENTION IN CONNECTOR BLOCK FOR IMPLANTABLE MEDICAL DEVICE

FIELD OF THE INVENTION

This invention relates to headers for coupling a lead for a tissue stimulating devices, such as a cardiac pacemaker or implantable cardioverter-defibrillator, to a pulse generator, and more particularly to a mechanical connector which incorporates a unique setscrew retention construction.

BACKGROUND OF THE INVENTION

Implantable medical tissue stimulators including pacemakers, defibrillators and neural stimulators are used to stimulate tissue such as cardiac tissue or spinal cord tissue with electrical pulses. Such tissue stimulators are now quite common and typically include a hermetically sealed housing or can containing an electronic circuit and power supply for producing electrical impulses under control of a programmed microprocessor. The pulse generator is connected to target tissue by means of a suitable medical lead. Such leads typically include an elongated flexible lead body having a proximal end and a distal end. Disposed at the distal end of the lead are one or more tissue contacting electrodes. The electrodes are connected by wires running through the lead body to associated contacts on a terminal pin at the proximal end of the lead.

The proximal lead terminal pin is adapted to be inserted into a longitudinal bore formed in a header of the stimulating pulse generator. Contained within the header are one or more conductive connector blocks that are connected to feedthrough pins that pass through hermetic seals to join with input and/or output nodes of the electronic circuit contained within the housing. The connector blocks will typically have apertures formed therethrough in alignment with the bore of the header, allowing the proximal lead terminal pin to be inserted through them. To lock the lead in place, the connector blocks will typically include a threaded bore that extends transverse to the longitudinal direction of the bore in the header. Setscrews are inserted into these threaded bores and tightened down against contact areas on the proximal lead terminal. In prior art connector block designs, from time to time the setscrew is accidentally backed out completely from the block and could not be re-inserted in to the block. Another equally problematic situation occurs when the lead is not inserted in the connector block and the setscrew is advanced to the extent that it falls into the longitudinal bore of the block which is an extension of the longitudinal lead receiving bore of the header.

U.S. Pat. No. 5,989,077 to Mast et al. provides an example of a header assembly of the type which the present invention seeks to avoid. Specifically, the header assembly serves for coupling a cardiac lead to a cardiac stimulator and employs a setscrew threadedly coupled to a connector housing of the header assembly but without provision for retaining it in place so that it neither backs out of the tapped bore in which it is received or advances too far in the absence of an end of a lead which it is intended to engage.

In U.S. Pat. No. 5,000,177 to Hoffmann et al., an implantable system is provided in which setscrews are confined within bores of the connector block against advancing too far but, notwithstanding the provision of plug seals over their heads, are capable of being backed away from their threaded condition.

In U.S. patent application Publication US 2004/0225334 to Persuitti et al., a connector block and its associated locking setscrew for an implantable electronic tissue stimulating device are designed to eliminate thread damage to the setscrew which is a cause of the setscrew becoming stuck in the connector block. In this disclosure, there is no concern presented for the problem addressed by the present invention.

It was in light of the foregoing that the present invention was conceived and has now been reduced to practice.

SUMMARY

A header assembly for coupling a medical electrical lead to a medical stimulating device includes a header having a first bore for receiving a proximal terminal pin of the lead. A connector block coupled to the header has a second bore aligned with the first bore and a tapped bore transverse of, and in communication with, the second bore, and the assembly includes a setscrew with mounting threads of defined length threadedly engaged with the tapped bore. The tapped bore has first and second tapped regions spaced by a smooth bore region which is longer than the length of the threaded portion of the setscrew. As the setscrew is tightened, it has already been threaded through the first tapped region and resides within the smooth bore region, and then becomes threadedly engaged with the second tapped region such that the tip end becomes firmly engaged with the proximal terminal pin of the medical electrical lead.

The invention is designed to provide retention features for the setscrew for both potential problematic situations. The setscrew will not be able to be advanced all the way in or backed out completely from the block. In short, the invention provides a redesigned setscrew and connector block with an internal feature to allow a setscrew to advance sufficiently to securely lock the lead in place but also prevent the setscrew to advance too far such that it advances beyond the threaded bore and into the connector block. Another benefit of the invention is that the construction prevents the setscrew from backing out completely from the connector block and falling outside the block.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENT

Figure 1:
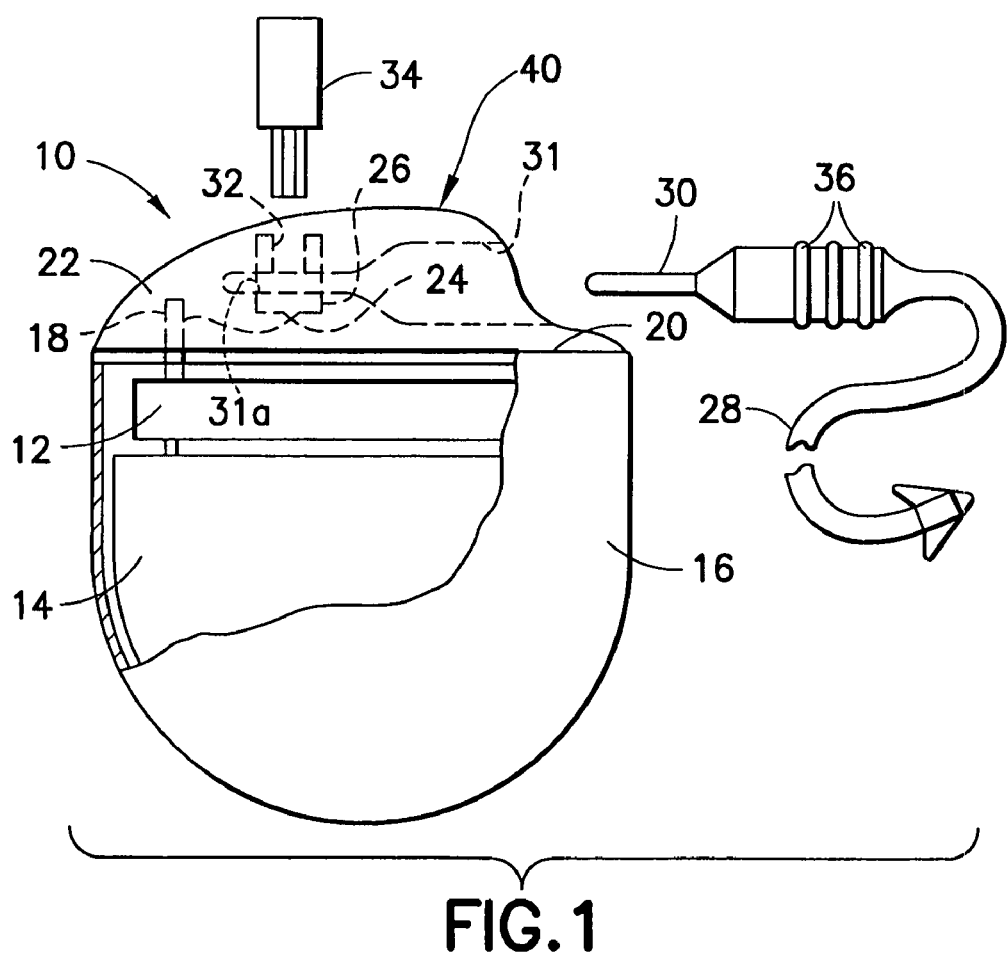
FIG. 1 is an exploded perspective view of an implantable medical device embodying the present invention, illustrating a sealed pacemaker housing and its associated header assembly, and an associated lead ready for insertion into a receiving channel of the connector.
Figure 2:
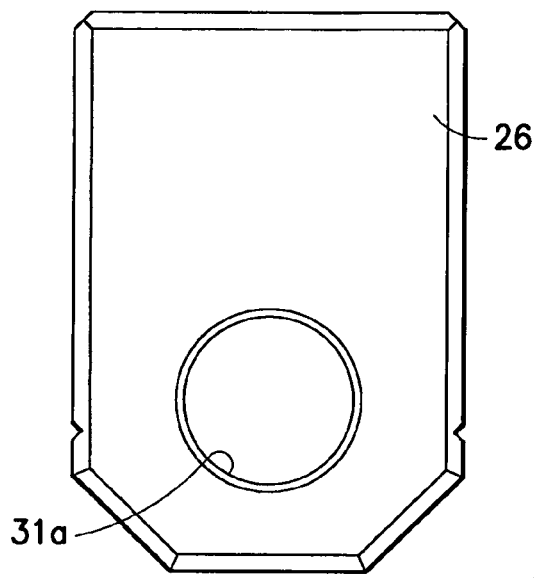
FIG. 2 is a side elevation view of a connector block which is one component of the present invention.
Figure 4:
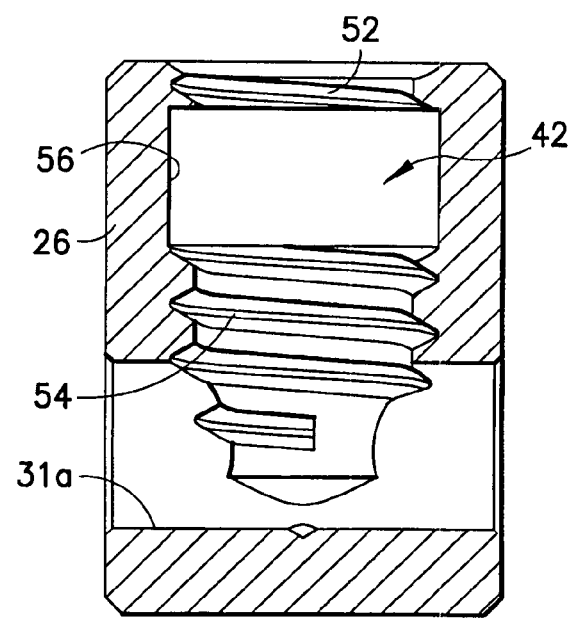
FIG. 4 is a cross section view taken generally along line 4-4 in FIG. 3.
Figure 3:
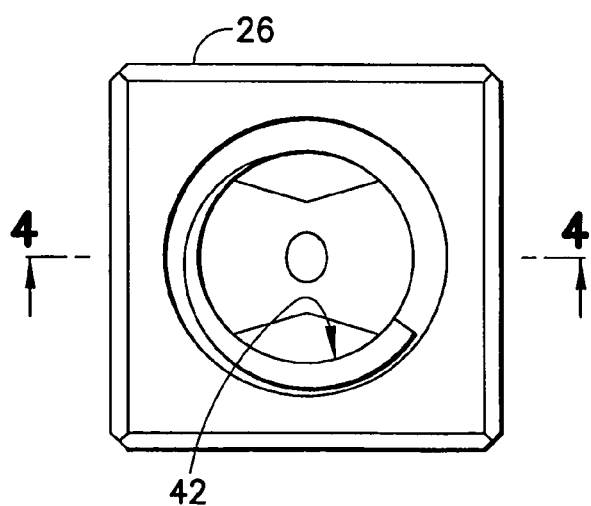
FIG. 3 is a top plan view of the connector block illustrated in FIG. 2.
Figure 5:
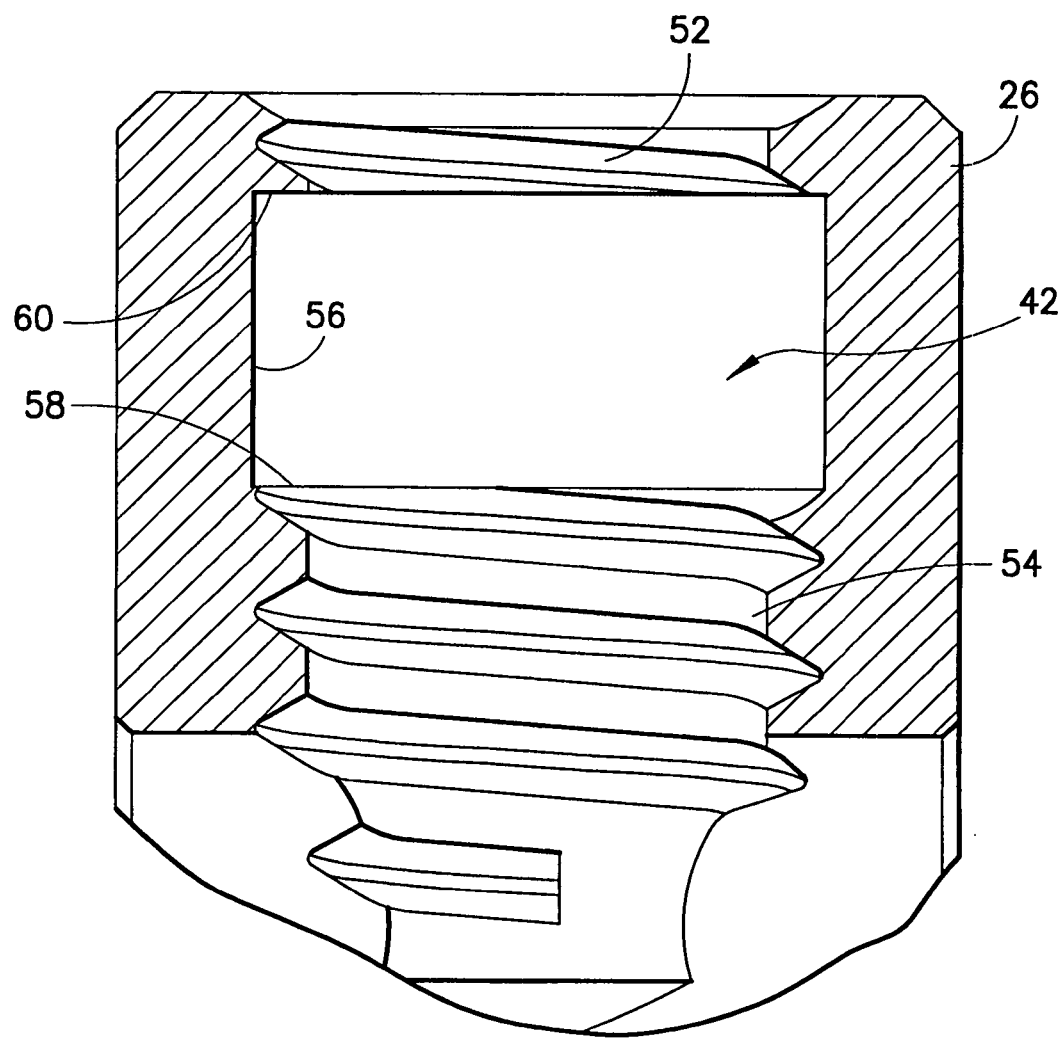
FIG. 5 is a detail cross section view, in elevation, illustrating in greater detail a portion of FIG. 4.
Figure 6:
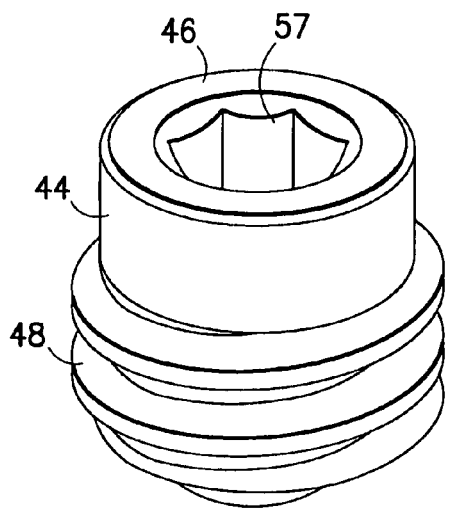
FIG. 6 is a perspective view of a setscrew which is another component of the present invention.
Figure 8:
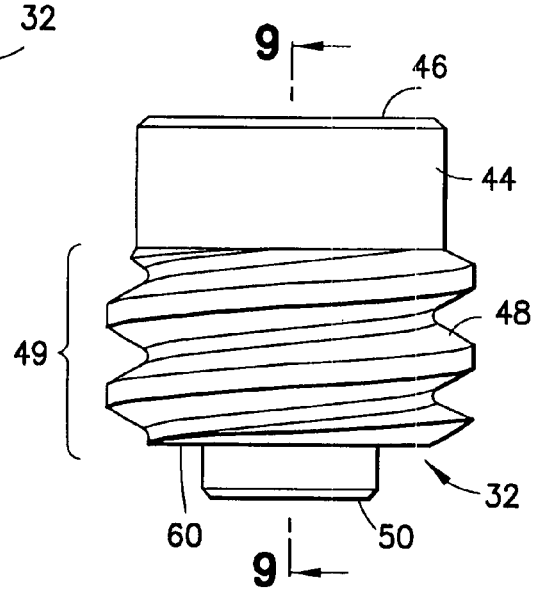
FIG. 8 is a side elevation view of the setscrew illustrated in FIGS. 6 and 7.
Figure 7:
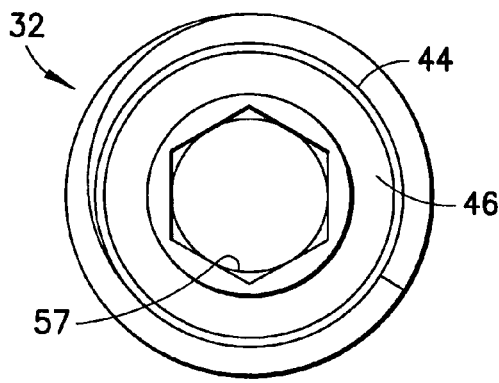
FIG. 7 is a top plan view of the setscrew illustrated in FIG. 6.
Figure 9:
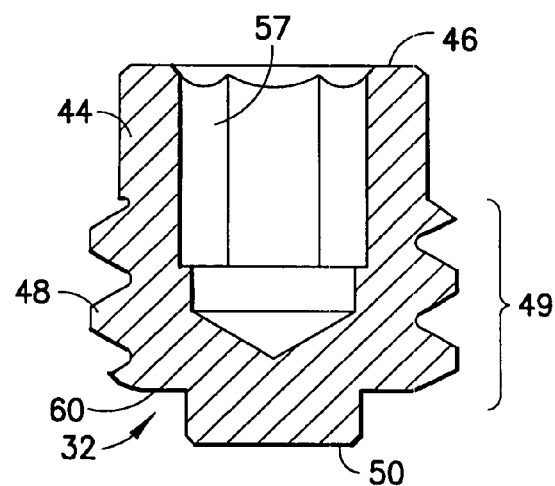
FIG. 9 is a cross section view taken generally along line 9-9 in FIG. 8.

Turn now to the drawings and, initially to FIG. 1 which generally illustrates, diagrammatically, an elevation view of a header assembly or connector system 40 for a sealed implantable medical device such as a cardiac stimulation device 16, possibly in the form of a pacemaker. Although the present invention will be described with reference to the embodiments shown in the drawings, it should be understood that the present invention can be embodied in many alternate forms or embodiments. In addition, any suitable size, shape or type of elements or materials may be used.

In order to appreciate the advantages of the present invention, it will help first to have a basic understanding of the manner in which the mechanical and electrical connection functions are carried out in known cardiac stimulation devices, a pacemaker here being exemplary. The main components associated with the connection function of such known pacemakers are shown diagrammatically in FIG. 1 but apply to the present invention as well. A pacemaker 10 electrically includes a battery 14 that powers electrical circuits 12. The pacemaker electrical circuits 12 and battery 14 are mechanically enclosed and hermetically sealed in a suitable housing 16. Typically, this housing or case 16 is shaped to include a flat side or platform 20 to which a suitable header assembly 22 can be mounted. At least one feedthrough terminal, 18, in electrical contact with the electrical circuits 12, passes through the case or housing 16 and protrudes beyond the platform 20. This feedthrough terminal 18 is electrically isolated from the case 16. A platinum wire 24, or other suitable conductive element, connects the terminal 18 to a conductive connector block 26 that is fitted within the header assembly 22. A pacemaker lead 28 having a proximal electrode or terminal pin 30 connects to the pacemaker electrical circuits by inserting the terminal pin 30 into a receiving channel or first bore 31 of the header assembly 22 until the terminal pin 30 is in contact with the connector block 26 by way of a block receiving channel or second bore 31a. A setscrew 32 is then securely tightened using a tool 34 such as a torque wrench to firmly hold the electrode 30 in both mechanical and electrical connection with the connector block 26. A septum, not shown but typically having the construction generally described in commonly assigned U.S. Pat. No. 5,509,928 issued Apr. 23, 1996 to Acken, may be placed over the setscrew 32 in order to prevent body fluids from seeping through the setscrew hole. Further, sealing ribs or ridges 36 on the connecting end of the pacemaker lead are designed to tightly engage the inside edges of the receiving channel 31 in order to prevent any body fluids from entering into the receiving channel 31 once the connecting end of the lead has been inserted into the header assembly 22.

While the descriptions presented in the prior art vary greatly relative to, for example, different types of locking mechanisms for performing the mechanical connection function, or different types of arrangements for performing the electrical feedthrough function, including the use of bipolar or multiple pacemaker leads, all such systems include the use of a pre-molded or cast header assembly 22 that is bonded to a sealed pacemaker housing 16 in which the electrical circuits are located.

Typically, prior art header assemblies 22 are cast in place from epoxy to the platform 20 of the pacemaker or, using more recent technology, a pre-molded header assembly may be mounted to the platform using a suitable sealing and bonding agent. Further, once the electrical connection is made from the terminal post 18 to the connector block 26, and the header assembly is attached to the housing, all remaining voids within the header 22, not including the receiving channel 31 into which the proximal end of the pacemaker lead 28 is to be inserted, must be filled with a suitable filler material, such as a two-component epoxy or silicone rubber.

It was earlier mentioned that the focus of the present invention is to provide retention features for the setscrew for a pair of potential problematic situations. By using the teachings of the invention, the setscrew 32 will not be able to be advanced all the way in or backed out completely from the connector block. For an explanation of the specifics of the invention, while continuing to view FIG. 1, turn now also to FIGS. 2 to 9.

As earlier noted, the connector block 26 (see FIGS. 2, 3, 4, and 5) is suitably coupled to the header assembly 22 and has the second bore 31a aligned with the first bore 31 and a tapped bore 42 provided in the connector block 26 has an axis transverse of, and in communication with, the second bore. Associated with the connector block is the setscrew 32 (see FIGS. 6, 7, 8, and 9) which extends from a mounting shank 44 at a head end 46 to mounting threads 48 of a defined length 49 adjacent a tip end 50. The tapped bore 42 of the connector block 26 has first and second tapped regions 52, 54, respectively, spaced by a smooth bore region 56 which is longer than the defined length 49 of the mounting threads 48 of the setscrew 32.

Figure 10:
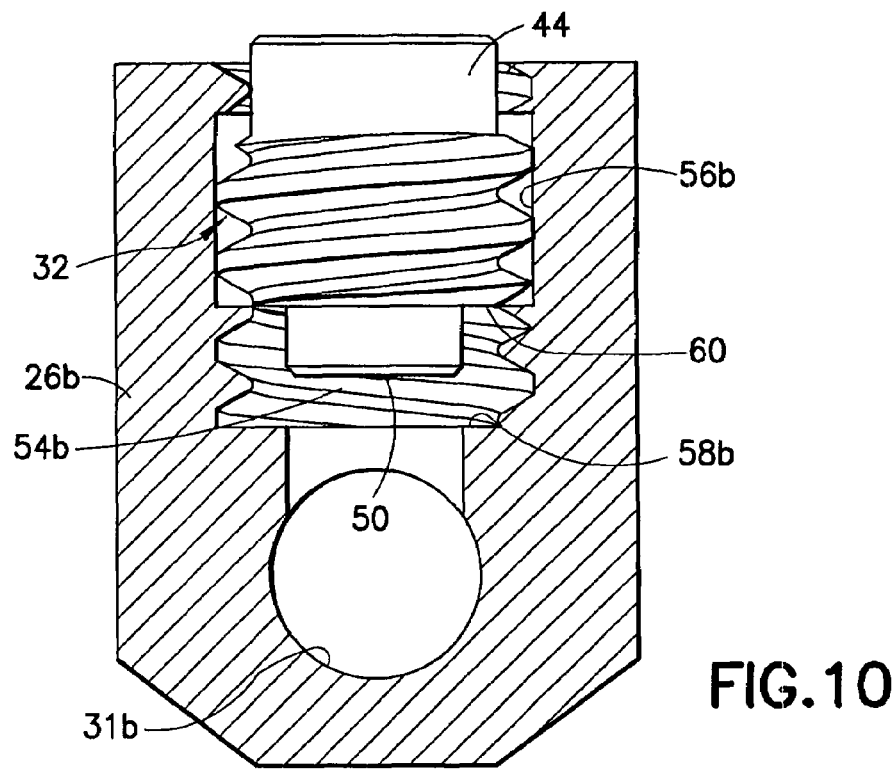
FIG. 10 is a side elevation view in section illustrating one relative position of the combination of the connector block and the setscrew of the invention.
Figure 11:
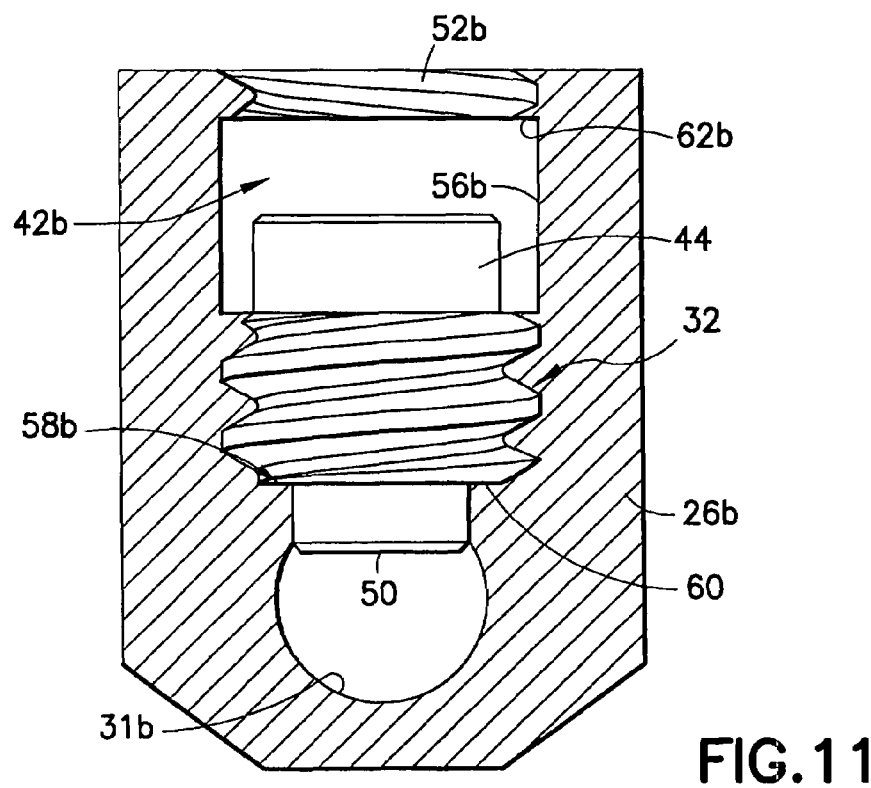
FIG. 11 is a side elevation view in section illustrating another relative position of the combination of the connector block and the setscrew of the invention.

Turn now to FIGS. 10 and 11 in addition to the prior figures. FIGS. 10 and 11 illustrate another embodiment of the connector block 26 and in this embodiment, the connector block is indicated by reference numeral 26b and all other components in this connector block embodiment are indicated by similar reference numerals with the suffix "b". The setscrew 32 is threadedly engaged with the tapped bore 42, 42b. The head end 46 of the setscrew 32 is formed, as at 57, to engageably receive the tool 34 (FIG. 1) for tightening the setscrew into engagement with the proximal terminal pin 30 of the medical electrical lead 28 and, alternatively, for withdrawing the setscrew from engagement with the proximal terminal pin of the medical electrical lead. With particular attention to FIGS. 10 and 11, it is seen that the connector block 26b has a square shoulder 58b at the interface between the second tapped region 54 and the second bore 31b engageable with a shoulder 60 of the setscrew 32 spaced from the tip end 50 to prevent the setscrew from advancing farther into the second bore. It will be understood that, in the instance of the connector block 26 of FIGS. 4 and 5, if the diameter of the bore 31a is larger than the length of the setscrew 32, the setscrew could advance until it deleteriously falls into the bore 31a. The altered construction of the connector block 26b illustrated in FIGS. 10 and 11 prevents this occurrence.

With this construction, as the setscrew 32 is tightened into engagement with the tapped bore of the connector block, it has already been threaded through the first tapped region 52, 52b and resides within the smooth bore region 56, 56b, and then becomes threadedly engaged with the second tapped region 54, 54b until the tip end 50 is firmly engaged with the proximal terminal pin 30 of the medical electrical lead 28 extending through the first bore 31 and into the second bore 31a, 31b. It will be appreciated that with the tip end 50 of the setscrew 32 engaged with the proximal terminal pin 30, a space will exist between the shoulder 60 of the setscrew and the square shoulder 58b of the connector block 26b. Should the proximal terminal pin 30 be removed from the bore 31b, the setscrew 32 can then be advanced but only to the extent that the shoulder 60 engages the square shoulder 58b and farther advance of the setscrew is halted.

Although the setscrew 32 can be loosened from its engagement with the proximal terminal pin 30, it can no longer leave the confines of the tapped bore 42, 42b because the tool 34 used for its initial advancement into the connector block 26, 26b is incapable of applying an oppositely directed force for its removal from the connector block. More specifically, the defined length 49 of the mounting threads 48 of the setscrew 32 is shorter than the length of the smooth bore region 56, 56b. With the setscrew freely residing within the smooth bore region, it would be necessary to pull the setscrew toward the first tapped region 52, 52b but the tool 34 has no such capability. Hence, once the setscrew 32 is advanced into the smooth bore region 56, 56b, it remains in the tapped bore 42, 42b for the life of the connector block unless extraordinary steps are taken.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A header assembly for coupling a medical electrical lead to an implantable medical device, the header assembly comprising:
   a connector block coupled to the header and having a first bore for receiving a proximal terminal pin of the medical electrical lead and a tapped bore transverse of, and in communication with, the first bore; and
   a setscrew comprising mounting threads of a defined length;
   the tapped bore having first and second tapped regions spaced by a smooth bore region which is longer than the defined length of the mounting threads.

2. A header assembly as set forth in claim 1
   wherein the head end of the setscrew is formed to engageably receive a tool for tightening the setscrew into engagement with the proximal terminal pin of the medical electrical lead and, alternatively, for withdrawing the setscrew from engagement with the proximal terminal pin of the medical electrical lead.

3. A header assembly as set forth in claim 1
   wherein the connector block has a square shoulder at the interface between the second tapped region and the first bore.

4. A header assembly as set forth in claim 3
   wherein the setscrew defines a tip end that extends distally from the mounting threads and configured to extend into the first bore.

5. A header assembly as set forth in claim 1
   wherein the connector block has a square shoulder at the interface between the first tapped region and the smooth bore region.

6. A connector system for use with a sealed implantable medical device having a medical electrical lead receiving bore for slidably receiving a proximal terminal pin of an electrical lead, the lead receiving bore having an open end for receiving the proximal terminal pin and a closed end, the connector system comprising:
   a pulse generator operative to generate electrical stimuli;
   a sealed housing containing the pulse generator;
   a header having a first bore for receiving the proximal terminal pin of the medical electrical lead;
   a connector block coupled to the header and having a second bore aligned with the first bore and a tapped bore transverse of, and in communication with, the second bore; and
   a setscrew extending from a mounting shank at a head end to mounting threads of defined length adjacent a tip end;
   the tapped bore having first and second tapped regions spaced by a smooth bore region which is longer than the defined length of the mounting threads of the setscrew; and
   the setscrew being threadedly engaged with the tapped bore.

7. A header assembly as set forth in claim 6
   wherein the head end of the setscrew is formed to engageably receive a tool for tightening the setscrew into engagement with the proximal terminal pin of the medical electrical lead and, alternatively, for withdrawing the setscrew from engagement with the proximal terminal pin of the medical electrical lead.

8. A header assembly as set forth in claim 6
   wherein the connector block has a square shoulder at the interface between the second tapped region and the second bore; and
   wherein the setscrew has a shoulder spaced from the tip end thereof engageable with the square shoulder of the connector block to prevent the setscrew from advancing farther into the second bore.

9. A header assembly as set forth in claim 6
   wherein the connector block has a square shoulder at the interface between the first tapped region and the smooth bore region.

10. In combination, a connector block and a lead-locking setscrew for use in a header of an implantable pulse generator, the header having a first bore for receiving a proximal terminal pin of a medical electrical lead, comprising:
    the connector block coupled to the header and having a second bore aligned with the first bore and a tapped bore transverse of, and in communication with, the second bore;
    a setscrew extending from a mounting shank at a head end to mounting threads of defined length adjacent a tip end;
    the tapped bore having first and second tapped regions spaced by a smooth bore region which is longer than the defined length of the mounting threads of the setscrew; and the setscrew being threadedly engaged with the tapped bore.

11. A header assembly as set forth in claim 10 wherein the head end of the setscrew is formed to engageably receive a tool for tightening the setscrew into engagement with the proximal terminal pin of the medical electrical lead and, alternatively, for withdrawing the setscrew from engagement with the proximal terminal pin of the medical electrical lead.

12. A header assembly as set forth in claim 10 wherein the connector block has a square shoulder at the interface between the second tapped region and the second bore; and
wherein the setscrew has a shoulder spaced from the tip end thereof engageable with the square shoulder of the connector block to prevent the setscrew from advancing farther into the second bore.

13. A header assembly as set forth in claim 10 wherein the connector block has a square shoulder at the interface between the first tapped region and the smooth bore region preventing engagement of the mounting threads of the setscrew with the first tapped region and thereby preventing the setscrew from being withdrawn from the connector block.

\* \* \* \* \*